United States Patent [19]

Teodorescu et al.

[11] Patent Number: 4,499,186

[45] Date of Patent: Feb. 12, 1985

[54] DIAGNOSING AUTOIMMUNE RHEUMATOID ARTHRITIS BY MEASURING PROTEOLYTIC ACTIVITY OF $\alpha_2$-MACROGLOBULIN

[75] Inventors: Marius C. Teodorescu, Westchester; Alexander M. Gaspar, Chicago; Gregory T. Spear, Forest Park; Doina Ganea, Elmhurst; John L. Skosey, Chicago, all of Ill.

[73] Assignee: University of Illinois, Board of Trustees, Urbana, Ill.

[21] Appl. No.: 454,788

[22] Filed: Dec. 30, 1982

[51] Int. Cl.³ ............... G01N 33/52; G01N 33/68; G01N 33/50
[52] U.S. Cl. .................................. 435/23; 435/4; 435/7; 435/213; 435/810; 436/506; 436/509; 436/529; 436/825
[58] Field of Search ............... 435/4, 7, 23, 213, 810; 422/61; 436/506, 509, 529, 808, 825

[56] References Cited

U.S. PATENT DOCUMENTS 4,221,706 9/1980 Ali ........................ 435/23 X
4,314,936 2/1982 Yaron ..................... 435/24 X
4,402,934 9/1983 Teodorescu ............. 435/810 X

FOREIGN PATENT DOCUMENTS 48989 4/1982 European Pat. Off. .

OTHER PUBLICATIONS

Chemical Abstracts I, 91:189040f (1979).
Chemical Abstracts II, 93:234464b (1980).
W. Cullman et al., J. Clin. Chem. Clin. Biochem., 19, 287-290 (1981).
T. Sipos et al., Biochem., 9(14), 2766-2775 (1970).

Primary Examiner—Sidney Marantz
Attorney, Agent, or Firm—Philip Hill

[57] ABSTRACT

A method for diagnosis of rheumatoid arthritis and related autoimmune diseases comprises blocking calcium ions contained in a blood sample, effecting hydrolysis of a selected substrate in the presence of $\alpha_2$-macroglobulin ($\alpha_2$M) from the blood sample, and determining the extent of hydrolysis of the substrate. Preferably, $\alpha_2$M in plasma is incubated with a hydrolyzable chromogenic substrate and the liberated chromogen is determined spectrophotometrically. A diagnostic kit is also provided.

21 Claims, No Drawings

DIAGNOSING AUTOIMMUNE RHEUMATOID ARTHRITIS BY MEASURING PROTEOLYTIC ACTIVITY OF $\alpha_2$-MACROGLOBULIN

BACKGROUND OF THE INVENTION

The invention described herein was made in the course of work supported in part by NCI Grant CA 21399 and in part by NIH Grant AM 28469.

It is well-known that some diseases have an autoimmune pathogenetic mechanism. Among these are rheumatoid arthritis, systemic lupus erythematosus, and chronic active hepatitis. A general increase in the level of gammaglobulins (antibodies) often accompanies an increase in the level of a particular antibody or antibodies in patient serum. These observations have led to the suggestion that polyclonal (general) activation of B-lymphocytes is involved in the disease process and might even precede the emergence of a particular antibody. For example, in rheumatoid arthritis the symptoms may appear before the characteristic antibody, i.e., the rheumatoid factor, develops.

On the other hand, other arthritides are known to have no systemic autoimmune basis and are commonly described as "sero-negative". These include Reiter's syndrome, ankylosing spondylitis, psoriatic arthritis, osteo-arthritis, and gout.

In each autoimmune disease the presence of one or several antibody specificities has been observed, but the presence of an antibody in the absence of disease has also been reported, particularly in elderly patients. Under these circumstances the role of antibodies in some autoimmune diseases has always been questionable, although they are currently used as disease indicators.

Another feature of autoimmune diseases is the presence of immune complexes, which, under certain conditions can activate the complement cascade. For example, it is usual for serum complement to be activated in systemic lupus erythematosus but very unusual in rheumatoid arthritis, although immune complexes have been described in both diseases. The immune complexes are expected to fix complement, resulting in the activation of proteolytic enzymes.

Aside from other proteases, two major systems generate proteolytic enzymes: the complement system mentioned above and the coagulation system. Most if not all of the enzymes of these two systems are known to require calcium ion ($Ca^{++}$) for their function.

Another property of the proteolytic enzymes found in the serum is their ability to bind to $\alpha_1$ antitrypsin, which inactivates the enzyme, or to $\alpha_2$-macroglobulin ($\alpha_2M$). The $\alpha_2M$ is capable of binding the proteases but the active site remains free to act. The only restriction is that while the free enzyme can degrade both high and low molecular weight substrates, the enzyme bound to $\alpha_2M$ can only degrade low molecular weight substrates. At the same time the free enzymes are blocked by large-molecule inhibitors such as soybean trypsin inhibitor (SBTI, m.w. 21,000) as well as by low-molecule weight inhibitors such as aprotinin, phenyl-methyl-sulfonyl-fluoride, or diisopropyl phosphofluoridate. It appears that SBTI has some inhibitory effect on $\alpha_2M$-bound trypsin but it is much less effective than the low m.w. inhibitors.

It has been reported in *Int. J. Immunopharmac.*, vol. 4, no. 1, pp. 1–7 (1982), that an $\alpha_2M$-associated factor is produced in cultures of rabbit lymphoid cells. This factor (or lymphokine) has the ability to activate B lymphocytes, i.e., it was a polyclonal B-cell activator (PBA). Its activating effect was blocked by low m.w. protease inhibitors but not by SBTI. This PBA behaved as a trypsin-$\alpha_2M$ complex. In the next step $\alpha_2M$ was extracted from patient serum and from normal human serum and employed in determining directly the activity for tosyl-arginyl-methylester (TAME). The absorption at 247 nm after 30 min. at 37° C. was determined. Slightly more proteolytic activity was observed with purified $\alpha_2M$ from patient serum.

There remains a need for the determination of the proteolytic activity associated with $\alpha_2M$ directly in human blood. Many problems are certain to be encountered in such a program. For example, there are many proteases in the serum, particularly from the coagulation system, that can bind to $\alpha_2M$; thus serum cannot be used. If $Ca^{2+}$ blocking agents are used to obtain plasma, the enzyme may not be functional. If SBTI is used to block free proteases in plasma, it may slow and alter significantly the enzyme activity associated with $\alpha_2M$. If $\alpha_2M$ is first attached to a solid phase or is precipitated by an antibody, it may carry with it proteases from complement or the coagulation system. No technique is readily suggested by the prior art and, indeed, it would appear from that art that the measurement of any significant amount of enzyme activity would not be possible because of difficulties in obtaining plasma suitable for the purpose.

SUMMARY OF THE INVENTION

This invention provides a novel method for diagnosing rheumatoid arthritis and related autoimmune diseases in a patient, comprising the steps of:
(a) collecting a sample of patient's blood in the presence of a stoichiometric excess of a calcium-ion blocking reagent, to provide a representative portion of $\alpha_2$-macroglobulin in plasma;
(b) mixing the $\alpha_2$-macroglobulin with a buffered hydrolyzable substrate;
(c) incubating the mixture; and
(d) determining the degree of hydrolysis of the substrate during incubation.

It is an object of this invention to provide a reliable method for the early diagnosis and detection of rheumatoid arthritis.

It is a further object of this invention to provide a convenient and inexpensive method for the ascertainment of the presence of absence of rheumatoid arthritis.

It is a still further object of this invention to provide diagnostic means, in the form of an assay kit, for the ready determination of the presence of rheumatoid arthritis in a patient, and adapted for use in the hands of a suitably trained clinical laboratory assistant.

DESCRIPTION OF THE INVENTION

Earlier investigations, included in part in U.S. patent application Ser. No. 202,117, filed Oct. 30, 1980, now U.S. Pat. No. 4,402,934, identified the factor known as polyclonal B-cell activator (PBA) with a protease associated with $\alpha_2$-macroglobulin ($\alpha_2M$) present in blood plasma. A simple colorimetric test has now been discovered whereby it most surprisingly becomes possible to employ blood plasma directly in an assay technique uniquely capable of identifying the presence of rheumatoid arthritis. This is a particularly valuable invention in that it now becomes possible to detect incipient rheumatoid arthritis prior to the appearance of any physical symptoms. This is a particularly unexpected development inasmuch as many proteases are present in the blood stream.

Blood plasma, having its calcium ion (Ca++) content blocked, is mixed with a protease substrate containing a selected amino acid, preferably arginine, in association with a chromogenic moiety. Enzyme attack under incubation conditions releases the chromogen in response to the effective proteolytic environment. Chromogen concentration is determined by measuring absorption at an appropriate wavelength.

Alternatively, immunoadsorption of $\alpha_2M$ on a surface, treated first with an antibody, followed by contact with the protease substrate and incubation, leads to a comparably unique result.

This inventive method lends itself especially well to affordance of an assay kit, containing appropriately stored substrate, buffer and calcium ion-blocking compositions, disposable cuvettes adapted for sampling and for spectrophotometric measurements, collection tubes, and antibody-coated solid phase. Such a kit is inexpensive, operable in the hands of a suitably trained clinical laboratory assistant, and particularly suitable for clinical use where numerous tests over a relatively short period of time are in order.

Basically, the method of this invention may be described as comprising the steps of:
(a) collecting a sample of patient's blood in the presence of a stoichiometric excess of a calcium-ion blocking reagent, to provide a representative portion of $\alpha_2$-macroglobulin in plasma;
(b) mixing the $\alpha_2$-macroglobulin with a buffered hydrolyzable substrate;
(c) incubating the mixture; and
(d) determining the degree of hydrolysis of the substrate during incubation.

Alternatively the method of this invention may include the additional step of depositing $\alpha_2$-macroglobulin from calcium ion-blocked plasma upon a surface penetrated with an antibody therefor prior to mixing with the buffered hydrolyzable chromogenic substrate.

In the practice of this invention the blood sample taken from the patient or from a general donor may be employed while freshly drawn, or may be stored in frozen condition until it is convenient to conduct the tests set forth above. If stored, the sample is, of course, thawed and brought to ambient temperature prior to further processing.

The $\alpha_2$-macroglobulin ($\alpha_2$-M) is contained in the plasma which is recovered on a blocking agent for calcium ions prior to separation of red blood cells by centrifugation. Suitable blocking (or complexing agents) must be soluble in the plasma and typically include sodium citrate and sodium ethylenediamine-tetraacetate (EDTA). A preferred reagent is sodium citrate.

The substrate composition includes a buffer, or buffers, capable of maintaining the pH value within the range from about 7 to about 9. Preferred buffer reagents include a phosphate saline solution (pH, 7.2) and the more elegant tris-buffer, tris (hydroxymethyl) aminomethane (pH, 8.2). The substrate also comprises a low molecular weight polyamide which incorporates a chromogenic moiety. Preferred substrates comprise an arginine compound, of which preferred examples include carbobenzoxy-valine-glycine-arginine-p-nitranilidacetate CHROMOZYM TRY ® and benzoylarginine-p-nitranilid (BAPNA). The substrate must be hydrolyzable and capable of yielding a chromogen (colored component) upon hydrolysis. Although p-nitroanilid constitutes a suitable and preferred chromogen, this invention contemplates other equally suitable chromogens. When employing p-nitroanilid, absorption measurements are preferably made at 380 nanometers (nm), equivalent to 3800 Ångstrom units.

The incubation period, during which the proteolytic activity occurs, may vary from about 1 up to about 24 hours, but is preferably held to 2 hours. Experience has shown this to be an adequate period for effective hydrolysis to occur. The incubation mixture may be frozen and stored, preferably at about $-20°$ C. until a suitable time for absorption measurement.

In the alternate embodiment of the method of this invention, any convenient solid surface material may be employed. In a preferred embodiment, Sepharose beads are employed. Distributed upon the selected surface material may be any suitable antibody. However, a preferred choice is rabbit IgG anti-human antibodies.

Although many variations of the identified parameters can lead to proper diagnosis, one preferred procedure of the method of this invention is set forth below.

Plasma is collected in tubes containing an anti-coagulant, preferably sodium citrate (0.3 mg/ml of blood). Within two hours after collection the blood is centrifuged, the plasma removed and either is immediately used or is stored frozen at $-25°$ until used. From each plasma sample 0.1 ml is diluted with 0.3 ml of phosphate buffered saline (PBS) pH 7.2. From this solution 0.1 ml is taken and mixed with 0.4 ml of 0.5M tris/HCl buffer at pH 8.2 and 0.1 ml of substrate containing 0.1 mg of CHROMOZYM TRY ® or 0.2 ml containing 0.042 mg of BAPNA. The mixture is incubated for 2 hours at 25° C. Higher or lower temperatures can also be used, but all conditions must be adjusted accordingly. As controls, two other mixtures are incubated; one in which the chromogenic substrate is substituted by an equal volume of solvent and one in which the plasma is substituted with buffered saline solution.

After two hours of incubation, the absorption (A) at 380 nm is determined in a spectrophotometer for all three samples. (Each sample may be prepared in triplicate). The absorbtion values obtained with plasma from patients with RA are significantly higher than those obtained with normal human plasma or plasma from patients with arthritides of non-autoimmune origin.

The following data, descriptive of biological techniques and test results, are exemplary, without limitation, of the method of this invention.

EXAMPLE I

Using heparin as an anti-coagulant, blood samples were obtained from 12 patients diagnosed as having rheumatoid arthritis (RA) and 10 normal patients. Plasma was collected by centrifugation. To each 0.2 ml of plasma, containing $\alpha_2$-macroglobulin ($\alpha_2$M), 0.2 ml of Carbo-benzoxy-Val-Gly-Arg-p-nitranilid-acetate (CHROMOZYM TRY ®; 1 mg/ml) was added along with soybean trypsin inhibitor (SBTI) (0.1 mg/ml) to block the proteolytic activity of the free enzymes, and the mixture was incubated at 25° C. for 2 hours. To stop the reaction and to remove the serum proteins, the volume of the mixture was doubled with a 10% solution of trichloracetic acid (TCA). The precipitate formed was removed and the absorption at 405 nanometers (nm) was determined in a Beckman spectrophotometer. Obviously, if a radio-labelled substrate were to be used, the determination would have been done with a radioactivity counter. The values shown in Table I were generally higher in the patient group than in the normal but two normal individuals showed values as high as the patients with very active disease.

Although there was a statistically significant difference between the two groups the practical value of the test was very questionable. The high normal values were very likely due to the heparin-activated enzymes attacking the arginine in the substrate. Moreover, heparin has been reported to activate other enzymes of the coagulation system and makes a complex with the substrate.

The SBTI did not appear to block the "nonspecific" proteolytic activity developed in the heparinized plasma and did not help in revealing differences between patients and normals. Moreover, experiments showed that SBTI slowed down significantly the enzyme activity associated with $\alpha_2 M$.

In parallel, each sample of heparinized plasma was incubated with Sepharose beads coated with the IgG fraction of rabbit antihuman $\alpha_2 M$. After 1 hour incubation at 25° C., the beads were washed and the substrate, cromozym Try, was added (1 mg/ml). Referring again to Table I, there was a significant difference between the normal donors and the patients, i.e., the patient $\alpha_2 M$ immunoadsorbed to the beads had proteolytic activity, most probably by containing an enzyme. However, false positive reactions were also seen in this system, suggesting that the heparinized plasma was not useful.

EXAMPLE II

An attempt was made to detect the $\alpha_2 M$-associated protease directly in plasma in which $Ca^{2+}$ was blocked. The degradation of CHROMOZYM TRY ® was measured in whole plasma in which the blood was collected on different anticoagulants: heparin, Na citrate, or sodium ethylene diamine tetraacetate (EDTA), the last two used to block $Ca^{2+}$. Moreover, an attempt was made to determine the presence of nitranilid, the CHROMOZYM TRY ® degradation product, directly in plasma, without precipitating the other proteins.

The first experiment was done with human plasma obtained on citrate to which the $Ca^{2+}$ was added. After clotting, the serum was removed and its ability to degrade the CHROMOZYM TRY ® was determined as in Example I. The serum was diluted 1/48 with buffer and substrate (83 µg/ml). The mixtures were incubated for various periods of time, from 0 to 24 hours. In parallel, the substrate alone and serum alone were also incubated. As an additional control trypsin was also incubated with the substrate. The following observations were made.

1. The absorption of p-nitranilid was maximal at 380 nm, whether the serum proteins were present or not.
2. Blocking the $Ca^{2+}$ did not significantly affect the degradation of the substrate.
3. The "spontaneous" proteolytic activity was much higher when heparin was used instead of citrate.
4. SBTI was not needed as a block for free proteases when the $Ca^{2+}$ is blocked.
5. Between 0 and 2 hours incubation, the proteolytic activity in citrated plasma does not increase but increases thereafter; this activity can be arrested by freezing.

When the plasma was incubated with a solid phase containing anti-$\alpha_2 M$ antibody a large part of the proteolytic activity in the serum was found associated with the $\alpha_2 M$, as described above. Again this activity was not impaired when citrate was added, i.e., in the absence of $Ca^{2+}$.

EXAMPLE III

Degradation of protease substrates was studied with RA patients, normal individuals, and with patients having arthritides of non-autoimmune origin. The rationale was the following: Both RA patients and patients with arthritides of non-autoimmune origin had joint inflammation. If RA patients had proteolytic activity in the plasma and the others did not, this activity was not caused by the joint inflammation, i.e., by proteolytic enzymes released from the inflammatory process in the joints. Thus, the test would indicate autoimmunity and not joint inflammation.

Blood samples were collected on Na citrate (3.8 mg/ml final concentration) and the plasma collected within 2 hours at 25° C. and stored at $-20°$ C. After thawing, aliquots of 0.2 ml were diluted ¼ with buffer (pH 8.2) and cromozym Try (0.83 µg/ml/final), benzoyl-Arg-p-nitranilid (BAPNA) (0.0426 mg/ml final) or L-Leu-p-nitranilid (LPN, 0.83 µg/ml final) were added. After 2 hours of incubation at 25° C., the absorbance (A) at 380 nm was determined in a Beckman spectrophotometer. The values are expressed as $A_{380}$ units $\times 100 \times$ dilution factor in Tables II and III. To determine the specific activity, the A values of the substrate alone and of the plasma diluted in buffer were determined and subtracted.

The values obtained with cromozym Try on 8 RA patients ranged from 1,464 to 2,793 and for 10 normal individuals from 302 to 1336. All of the 8 patients with joint inflammation of non-autoimmune origin, (i.e. "seronegative") had A values close to the normal range, i.e., from 566 to 1,387. If 1,387 units is considered the upper limit of normals, all RA patients fell outside the normal range when tested with cromozym.

EXAMPLE IV

To determine whether the polyclonal B cell activator (PBA) is indeed associated with $\alpha_2 M$, the plasma was enriched in $\alpha_2 M$ by two sequential precipitations with polyethylene glycol (PEG). The plasma was adjusted to 4% PEG and the precipitate was removed by centrifugation or by filtration. This first precipitate contained enzymes involved in the coagulation process such as thrombin. As a result the absorption values of normal plasma, following the technique of Example III dropped significantly, as shown in Table IV. The supernatant was then adjusted to 12% PEG and again a precipitate was formed. This precipitate contained most of the $\alpha_2 M$ and several other proteins. The proteolytic activity for CHROMOZYM TRY ® and BAPNA in the $\alpha_2 M$ rich precipitate remained high, i.e., it appeared as if the activity was associated with $\alpha_2 M$.

To show even further that what was measured in whole plasma was $\alpha_2 M$-associated protease, the following experiment was performed. Plasma was incubated at 25° C. with Sepharose beads coated with rabbit IgG antihuman $\alpha_2 M$ and were washed three times. CHROMOZYM TRY ® was added (0.83 mg/ml, final) to the beads and the release of the chromogen was determined as before. Again, as shown in Table III, much more proteolytic activity was found with RA patient plasma than in normal plasma. In conclusion, the measurement of the proteolytic activity for substrates containing arginine in whole plasma, in the precipitate rich in $\alpha_2M$, or in the immunoadsorbed $\alpha_2M$, is an indicator of autoimmunity independent of joint inflammation.

EXAMPLE V

A determination was made as to whether the $\alpha_2M$ from RA patient plasma had more proteolytic activity than the $\alpha_2M$ from the plasma of patients with nonautoimmune arthritides or from normal donors. The $\alpha_2M$-associated proteolytic activity in patients and normal individuals was compared as follows: plasma from 7 RA patients, 5 patients with "non-autoimmune" anthritides and 5 normal individuals was collected on sodium citrate (3.8 mg/ml) and stored at $-20°$ C., Sepharose beads were coated with rabbit IgG anti-human $\alpha_2M$ antibodies by using cyanogen bromide. As a control, beads were coated with rabbit antihuman Ig-light chain antibodies. The beads were washed and mixed with plasma for 2 hours at 25° C. with continuous rocking, and washed again three times. To the washed beads a solution of 0.83 mg/ml (final concentration) of CHROMOZYM TRY® was added and the mixture was incubated at 25° C. for 2 hours. The beads were centrifuged and the supernatants were collected and read at $Å_{380}$. After subtracting the spontaneous degradation of the substrate in the presence of anti-Ig coated beads, the values are given in Table V as specific $\alpha_2M$-associated proteolytic activity. This type of test shows, again, that the proteolytic activity in the plasma of patients with RA is much higher and than that in the plasma of normal controls or patients with seronegative arthritides. Thus, this activity correlated again with the activation of the immune system and not with the presence of joint inflammation.

TABLE I

Degradation of Chromozym Try ® by plasma collected on heparin and soybean trypsin inhibitor and by $\alpha_2M$ attached to immunoabsorbent Sepharose beads.

| Patient or donor | Diagnosis | Absorbtion at 405 nm (units/dl) | |
|---|---|---|---|
| | | Whole plasma | Sepharose beads |
| 1 | Rheumatoid | 166 ± 2* | 128 ± 11 |
| 2 | Arthritis | 149 ± 7 | |
| 3 | | 47 ± 7 | 63 ± 5 |
| 4 | | 65 ± 5 | 112 ± 8 |
| 5 | | 252 ± 8 | 149 ± 8 |
| 6 | | 39 ± 1 | 74 ± 4 |
| 7 | | 60 ± 1 | 63 ± 1 |
| 8 | | 90 ± 3 | 85 ± 4 |
| 9 | | 46 ± 4 | 71 ± 6 |
| 10 | | 74 ± 3 | 68 ± 7 |
| 11 | | 75 ± 1 | 67 ± 4 |
| 12 | | 67 ± 1 | 67 ± 2 |
| 13 | Normal | 50 ± 5 | 57 ± 4 |
| 14 | | 40 ± 1 | 53 ± 2 |
| 15 | | 44 ± 2 | 51 ± 5 |
| 16 | | 58 ± 4 | 55 ± 2 |
| 17 | | 53 ± 1 | 50 ± 1 |
| 18 | | 56 ± 6 | 31 ± 0 |
| 19 | | 41 ± 1 | 70 ± 7 |
| 20 | | 56 ± 6 | 40 ± 4 |
| 21 | | 34 ± 4 | 35 ± 3 |
| 22 | | 51 ± 2 | 48 ± 4 |

*Standard error.

TABLE II

Degradation of two protease substrates by plasma from patients with rheumatoid arthritis (RA) ($A_{380}$/dl ± standard error)

| Patient | Substrate degraded | |
|---|---|---|
| | Chromozym Try ® | BAPNA |
| 1 | 2788 ± 51 | 667 ± 1 |
| 2 | 2793 ± 143 | 667 ± 1 |
| 3 | 1807 ± 114 | 457 ± 15 |
| 4 | 1713 ± 64 | 417 ± 23 |
| 5 | 1757 ± 121 | 405 ± 3 |
| 6 | 1728 ± 10 | 501 ± 1 |
| 7 | 1670 ± 48 | 397 ± 1 |
| 8 | 1944 ± 88 | 371 ± 10 |
| 9 | 1464 ± 60 | 501 ± 1 |
| 10 | 2433 ± 143 | 413 ± 27 |
| 11 | 1791 ± 189 | 158 ± 7 |
| 12 | 1996 ± 63 | 653 ± 20 |
| 13 | 1708 ± 63 | 643 ± 9 |
| 14 | 2354 ± 116 | 614 ± 12 |
| 15 | 1803 ± 186 | 370 ± 16 |
| 16 | 2093 ± 41 | 313 ± 41 |
| 17 | 2054 ± 100 | 480 ± 29 |
| 18 | 1721 ± 41 | 385 ± 10 |
| Median | C. Try 1,805 | 438 |
| Range | C. Try 1,464–2,793 | BAPNA 158–667 |

TABLE III

Degradation of two protease substrates by plasma from patients with non-autoimmune arthritides or normal donors ($A_{380}$/dl ± Standard error)

| Patient or donor | Diagnosis | Substrate degraded | |
|---|---|---|---|
| | | Chromozym Try ® | BAPNA |
| 1 | Gout | 566 ± 59 | 144 ± 21 |
| 2 | Gout | 1051 ± 135 | 346 ± 25 |
| 3 | Osteo-arthritis | 1279 ± 170 | 318 ± 7 |
| 4 | Psoriartic arthritis | 792 ± 149 | 192 ± 9 |
| 5 | Osteo-arthritis | 1378 ± 180 | 371 ± 25 |
| 6 | Osteo-arthritis | 1003 ± 133 | 65 ± 10 |
| 7 | Osteo-arthritis | 1342 ± 75 | 362 ± 13 |
| 8 | Osteo-arthritis | 715 ± 126 | 384 ± 64 |
| 1 | Normal | 742 ± 30 | 197 ± 5 |
| 2 | | 888 ± 19 | 163 ± 32 |
| 3 | | 701 ± 2 | 334 ± 2 |
| 4 | | 529 ± 140 | 82 ± 7 |
| 5 | | 302 ± 73 | 84 ± 1 |
| 6 | | 553 ± 23 | 175 ± 6 |
| 7 | | 430 ± 66 | 97 ± 14 |
| 8 | | 912 ± 82 | 89 ± 1 |
| 9 | | 1336 ± 32 | 156 ± 8 |
| 10 | | 918 ± 111 | 336 ± 7 |
| Patients: | median | C. Try 1,027 | 355 |
| | range | C. Try 566–1,387 | BAPNA 65–384 |
| Normals: | median | C. Try 722 | BAPNA 160 |
| | range | C. Try 302–1336 | BAPNA 82–336 |

TABLE IV

The degradation of cromozym by the plasma proteins precipitated with various concentrations of polyethylene glycol

| Plasma donor | Diagnosis | $A_{380}$ units/dl | | | |
|---|---|---|---|---|---|
| | | 0% PEG | 4% PEG | 12.5% PEG | Supernate |
| 1 | RA* | 2,371 | 648 | 158 | 270 |
| 2 | RA | 1,828 | 348 | 185 | 883 |
| 3 | RA | 1,488 | 248 | 237 | 777 |
| 4 | RA | 1,920 | 344 | 243 | 830 |
| 5 | Normal | 739 | 254 | 47 | 560 |

*RA: Rheumatoid Arthritis

TABLE V

Degradation of cromozym by α₂M and plasma from patients with RA, normal donors and patients with non-autoimmune arthritides.

| Plasma Donor | Diagnosis | $A_{380}$ units/ml Whole plasma | Beads[a] |
|---|---|---|---|
| 1 | RA [b] | 2788 | 1209 |
| 2 | RA | 2794 | 996 |
| 3 | RA | 1754 | 888 |
| 4 | RA | 2433 | 1142 |
| 5 | RA | 1058 | 228 |
| 6 | RA | 1451 | 457 |
| 7 | RA [c] | 1446 | 650 |
| 8 | Gout | 566 | 230 |
| 9 | Gout | 1051 | 274 |
| 10 | OA | 1387 | 294 |
| 11 | OA | 1003 | 216 |
| 12 | OA | 715 | 100 |
| 13 | Normal | 529 | 321 |
| 14 | Normal | 553 | 201 |
| 15 | Normal | 430 | 362 |
| 16 | Normal | 912 | 428 |
| 17 | Normal | 918 | 196 |

[a] Plasma was incubated at 25¼ C. for 1 hour with Sepharose beads coated with anti-α₂M antibodies.
[b] RA: rheumatoid arthritis.
[c] OA: osteo-arthritis.
Mean values for beads: RA 796
Non-autoimmune 223
Normal 302

We claim:

1. A method for diagnosing rheumatoid arthritis and related autoimmune diseases in a patient, comprising the steps of:
   (a) collecting a sample of patient's blood in the presence of a stoichiometric excess of a calcium-ion blocking reagent, to provide a representative portion of α₂-macroglobulin in plasma;
   (b) mixing the α₂-macroglobulin with a buffered hydrolyzable substrate;
   (c) incubating the mixture; and
   (d) determining the degree of hydrolysis of the substrate during incubation.

2. The method of claim 1 comprising the additional step of separating the plasma from the red blood cells prior to mixing with the buffered substrate.

3. The method of claim 1 wherein the substrate is a buffered hydrolyzable chromogenic substrate.

4. The method of claim 1 wherein the plasma is separated from the red blood cells, the plasma is thereafter mixed with a buffered hydrolyzable chromogenic substrate, and the amount of chromogen released in the mixture by hydrolysis during incubation is measured by spectrophotometric absorption at a selected wavelength.

5. The method of claim 1 comprising the additional step of depositing α₂-macroglobulin from calcium ion-blocked plasma upon a surface pretreated with an antibody therefor prior to mixing with the buffered hydrolyzable substrate.

6. The method of claim 1 wherein the blood sample is fresh blood.

7. The method of claim 1 wherein the blood sample has been stored in the frozen state prior to testing.

8. The method of claim 1 wherein the calcium ion-blocking reagent is sodium citrate.

9. The method of claim 1 wherein the calcium ion-blocking reagent is sodium ethylenediamine-tetraacetate.

10. The method of claim 1 wherein the buffer comprises a phosphate saline solution maintained at about pH 7.2.

11. The process of claim 10 wherein the buffer additionally comprises tris (hydroxymethyl) aminomethane and the solution is maintained at about pH 8.2.

12. The method of claim 3 wherein the chromogenic substrate contains arginine.

13. The method of claim 12 wherein the chromogenic substrate comprises carbobenzoxy-valine-glycine-arginine-p-nitranilid-acetate.

14. The method of claim 12 wherein the chromogenic substrate comprises BAPNA.

15. The method of claim 1 wherein the incubation is effected at 25° C. for about 2 hours and the mixture is thereafter stored at about −20° C. prior to analysis.

16. The method of claim 4 wherein the selected wavelength is 380 nanometers.

17. The method of claim 5 wherein the surface for deposition of α₂-macroglobulin comprises Sepharose beads.

18. The method of claim 5 wherein the antibody comprises rabbit IgG anti-human α₂M antibodies.

19. A diagnostic kit, for assay of esterolytic activity of chromogenic substrates in the presence of α₂-macroglobulin, as a determinant for rheumatoid arthritis in a subject patient, comprising:
   (a) packaged sodium citrate solution, for receiving blood containing α₂-macroglobulin;
   (b) separately packaged hydrolyzable chromogenic substrate, containing arginine at the point of enzymatic attack, for reaction with α₂-macroglobulin; and
   (c) separately packaged cuvettes, containing buffer solution and adapted for incubation and use in analysis.

20. The diagnostic kit of claim 19 additionally comprising packaged aliquots of Sepharose beads coated with rabbit IgG anti-human α₂M antibodies.

21. The diagnostic kit of claim 19 wherein the cuvettes are adapted for insertion into a spectrophotometer.

* * * * *